(12) United States Patent
Suzuki et al.

(10) Patent No.: US 6,656,682 B1
(45) Date of Patent: Dec. 2, 2003

(54) NUCLEIC ACID-IMMOBILIZED SUBSTRATE

(75) Inventors: Osamu Suzuki, Chiba (JP); Tatsuo Ichihara, Chiba (JP); Namiko Shiohata, Chiba (JP); Yoshiyuki Matsumura, Chiba (JP)

(73) Assignee: Nisshinbo Industries, Inc., Tokyo (JP)

( * ) Notice: Subject to any disclaimer, the term of this patent is extended or adjusted under 35 U.S.C. 154(b) by 0 days.

(21) Appl. No.: 09/599,032

(22) Filed: Jun. 20, 2000

(30) Foreign Application Priority Data

Jun. 21, 1999 (JP) .......................................... 11-173966

(51) Int. Cl.⁷ ......................... C12Q 1/68; C12P 19/34; C12M 1/34; C07H 21/02; C07H 21/04
(52) U.S. Cl. ....................... 435/6; 435/7.1; 435/91.1; 435/91.2; 435/287.2; 536/22.1; 536/23.1; 536/24.3; 536/24.31; 536/24.32; 536/24.33
(58) Field of Search .................... 536/26.6, 24.3–24.33, 536/22.1, 23.1; 435/6, 7.1, 91.1, 91.2, 287.2

(56) References Cited

U.S. PATENT DOCUMENTS

| 5,622,826 | A |   | 4/1997 | Varma |
| 5,760,130 | A |   | 6/1998 | Johnston |
| 6,017,742 | A |   | 1/2000 | Takenishi |
| 6,077,673 | A | * | 6/2000 | Chenchik et al. |

FOREIGN PATENT DOCUMENTS

| EP | 0 710 666    | 5/1996  |
| EP | 1 001 267    | 5/2000  |
| JP | 8-23975      | 1/1996  |
| JP | 8-334509     | 12/1996 |
| WO | WO 95/35505  | 12/1995 |
| WO | WO 97/10365  | 3/1997  |

\* cited by examiner

Primary Examiner—Jeffrey Siew
(74) Attorney, Agent, or Firm—Kilpatrick Stockton LLP

(57) ABSTRACT

A nucleic acid-immobilized substrate which comprises a carrier comprising a base material and a compound having a carbodiimide group or an isocyanate group carried by the base material, and the same kind or different kinds of nucleic acids immobilized in the form of dots through the carbodiimide group or the isocyanate group at a plurality of sites on the carrier.

4 Claims, No Drawings

NUCLEIC ACID-IMMOBILIZED SUBSTRATE

BACKGROUND OF THE INVENTION

The present invention relates to a nucleic acid-immobilized substrate. More specifically, the present invention relates to a nucleic acid-immobilized substrate in which nucleic acids are securely immobilized on a carrier in the form of fine dots, useful as a DNA array and so forth.

Currently, the following two methods are mainly used for the preparation of a nucleic acid-immobilized substrate in which wherein nucleic acids are immobilized as fine dots on a carrier, for use as a DNA chip, DNA array or the like:

(1) a method utilizing immobilization of nucleic acids by physical adsorption on a base material coated with poly-L-lysine, which is used as a carrier (WO95/35505, International Patent Publication in Japanese (Kohyo) No. 10-503841/1998), and (2) a method comprising DNA synthesis on a base material (WO97/10365).

However, a nucleic acid-immobilized substrate manufactured by the above method (1) has a drawback that, when it is used for hybridization, nucleic acids may be dropped off from the substrate, in particular, during operation processes, which leads to reduction of detection sensitivity, fluctuation of results, i.e., a problem of reproducibility and so forth. Further, as for the efficiency in immobilization of nucleic acids by the method (1), it has a drawback that short nucleic acids of about 300-mer or less such as oligomers cannot be immobilized efficiently, although longer nucleic acids can be immobilized without any particular problems.

Further, the above method (2) requires special apparatuses and reagents for synthesizing DNA on a base material and cannot be readily employed by everyone. Further, nucleic acids to be synthesized are limited to those of about 25-mer or less. Furthermore, nucleic acids longer than 10-mer cannot so easily be synthesized.

Thus, the conventional methods have problems not only of having difficulty in preparing a nucleic acid-immobilized substrate to immobilize nucleic acids of from 10-mer to 300-mer, but also of being unable to securely immobilize nucleic acids of other lengths or being unable to immobilize nucleic acids by using a simple apparatus.

SUMMARY OF THE INVENTION

The present invention has been accomplished from the above viewpoints, and an object thereof is to provide a nucleic acid-immobilized substrate in which nucleic acids are securely immobilized on a carrier in the form of fine dots irrespective of their length, and which can be prepared by using a simple apparatus.

As a result of efforts dedicated by the present inventors to achieve the above object, it was found that, if nucleic acids were immobilized through a carbodiimide group on a carrier composed of a base material carrying a compound having the carbodiimide group, nucleic acids could be securely immobilized on the carrier in the form of fine dots irrespective of their length. Also, it was found that, if nucleic acids were immobilized through an isocyanate group on a carrier composed of a base material carrying a compound having the isocyanate group, nucleic acids could be securely immobilized on the carrier in the form of fine dots irrespective of their length. Thus, the present invention has been accomplished.

The followings are provided by the present invention.

(1) A nucleic acid-immobilized substrate which comprises a carrier comprising a base material and a compound having a carbodiimide group carried by the base material, and the same kind or different kinds of nucleic acids immobilized in the form of dots through the carbodiimide group at a plurality of sites on the carrier (also referred to as "carbodiimide carrier" hereafter).

(2) The nucleic acid-immobilized substrate according to (1), wherein the dots each have a substantially circular shape and a diameter of from 10 to 3000 $\mu$m.

(3) The nucleic acid-immobilized substrate according to (1), wherein the nucleic acids have a chain length of from 10 to 300 nucleotides.

(4) The nucleic acid-immobilized substrate according to (1), wherein the compound having the carbodiimide group is carried on a surface of the base material through a covalent bond.

(5) The nucleic acid-immobilized substrate according to (1), wherein number of the dots in which nucleic acids are immobilized is 10 to 10,000 per $cm^2$ of the substrate.

(6) A nucleic acid-immobilized substrate which comprises a carrier comprising a base material and a compound having an isocyanate group carried by the base material, and the same kind or different kinds of nucleic acids immobilized in the form of dots through the isocyanate group at a plurality of sites on the carrier (also referred to as "isocyanate carrier" hereafter).

(7) The nucleic acid-immobilized substrate according to (6), wherein the dots each have a substantially circular shape and a diameter of from 10 to 3000 $\mu$m.

(8) The nucleic acid-immobilized substrate according to (6), wherein the nucleic acids have a chain length of from 10 to 300 nucleotides.

(9) The nucleic acid-immobilized substrate according to (6), wherein the compound having the isocyanate group is carried on a surface of the base material through a covalent bond.

(10) The nucleic acid-immobilized substrate according to (6), wherein number of the dots in which nucleic acids are immobilized is 10 to 10,000 per $cm^2$ of the substrate.

According to the present invention, there is provided a nucleic acid-immobilized substrate in which DNAs are stably immobilized. Since nucleic acids can be immobilized on the substrate of the present invention without any limitation concerning the number of chains or the length of nucleic acids, various kinds of nucleic acids can simultaneously be handled on the same base material.

Furthermore, since nucleic acids are securely bound to the carrier through covalent bonds, the nucleic acid-immobilized substrate can be useful for use as a DNA chip of excellent reproducibility and quantification characteristics.

DETAILED DESCRIPTION OF THE INVENTION (1) Carrier

The carrier used for the nucleic acid-immobilized substrate of the present invention is provided for immobilizing nucleic acids and comprises a base material and a compound having a carbodiimide group or an isocyanate group (also referred to simply as "carbodiimide compound" or "isocyanate compound" hereafter, respectively) carried by the base material.

A. Carbodiimide Carrier (1) Base Material

The base material used for the present invention serve's as a support for the aforementioned carrier and is not particularly limited so long as it is basically insoluble in a solvent and is in a solid or gel state at an ordinary temperature or within a temperature range around the ordinary temperature (0 to 100° C.). The expression that the base material is insoluble in a solvent means that the base material is substantially insoluble in various solvents such as aqueous solvents and organic solvents used in various processes when the carbodiimide compounds are provided on the base material and nucleic acids are immobilized on the base material as a carrier, as will be described later, and then it is used as, for example, a DNA chip.

Materials used for such a base material of the carrier include, specifically, plastics, inorganic polymers, metals, natural polymers, ceramics and the like.

Examples of the plastics include, specifically, polyethylene, polystyrene, polycarbonate, polypropylene, polyamide, phenol resin, epoxy resin, polycarbodiimide resin, polyvinyl chloride, polyvinylidene fluoride, polyethylene fluoride, polyimide, acrylic resin and so forth. Examples of the inorganic polymers include glass, quartz, carbon, silica gel, graphite and so forth. Examples of the metals include metals that are solid at an ordinary temperature such as gold, platinum, silver, copper, iron, aluminum, magnet and paramagnet. Examples of the natural polymers include cellulose, cellulose derivatives, chitin, chitosan, alginic acid, alginic acid salts and so forth. Examples of the ceramics include apatite, alumina, silica, silicon carbide, silicon nitride, boron carbide and so forth.

The base material can be in the form of, for example, film, flat plate, fiber or the like. The size is not particularly limited.

(2) Compound having a carbodiimide group

The compound having a carbodiimide group used for the present invention include, for example, polycarbodiimides that can be prepared by the method disclosed in Japanese Patent Application Laid-open (Kokai) No. 51-61599(1976), the method of L. M. Alberino et al. (J. Appl. Polym. Sci., 21, p.190 (1990)), the method disclosed in Japanese Patent Application Laid-open (Kokai) No. 2-292316(1990) or the like, low molecular-weight carbodiimides such as monocarbodiimide and dicarbodiimide that are synthesized by a method generally used for carbodiimide production, such as dehydration of urea and desulfation of thiourea and so forth.

Specifically, the aforementioned polycarbodiimides can be prepared in the presence of a catalyst promoting carbodiimidation of isocyanate from an organic polyisocyanate compound (for example, 3-methyl-1-phenyl-2-phospholene-1-oxide).

Examples of the aforementioned organic polyisocyanate compound used for the preparation of the polycarbodiimides include, for example, 4,4'-dicyclohexylmethane diisocyanate, m-tetramethylxylylene diisocyanate, 2,4-tolylene diisocyanate, 2,6-tolylene diisocyanate, a mixture of 2,4-tolylene diisocyanate and 2,6-tolylene diisocyanate, crude tolylene diisocyanate, crude methylenediphenyl diisocyanate, 4,4',4"-triphenylmethylene triisocyanate, xylene diisocyanate, hexamethylene-1,6-diisocyanate, lysine diisocyanate, hydrogenated methylenediphenyl diisocyanate, m-phenyl diisocyanate, naphthylene-1,5-diisocyanate, 4,4'-biphenylene diisocyanate, 4,4'-diphenylmethane diisocyanate, 3,3'-dimethoxy-4,4'-biphenyl diisocyanate, 3,3'-dimethyldiphenylmethane-4,4'-diisocyanate, isophorone diisocyanate and a mixture of any of these.

Polycondensation occurs upon carbodiimidation of an isocyanate group in the aforementioned polyisocyanate compounds or their mixture. In this reaction, molecular weight (polymerization degree) of the product can be controlled by adding one or more kinds of monoisocyanate in an appropriate amount at an appropriate stage to block the terminals of the carbodiimide compound. The monoisocyanate can also be added in an appropriate amount at the beginning of the polycondensation reaction. Examples of such monoisocyanate include phenyl isocyanate, (ortho, meta or para)-tolylisocyanate, dimethylphenyl isocyanate, n-butyl isocyanate, cyclohexyl isocyanate, methyl isocyanate and so forth. The polymerization degree can also be controlled by the concentration of the polyisocyanate compound or the like or the reaction time.

The terminal blocking agent may be one that can be derived from a compound having isocyanate at a terminus easily prepared by a reaction of about 1 mole of a compound having an alkyl group containing a functional group such as —OH, —NH$_2$, —COOH, —SH or —NH at its terminus with 2 moles of aromatic diisocyanate.

Various kinds of substances can be mentioned as the catalyst for promoting carbodiimidation of the organic isocyanate. However, 1-phenyl-2-phospholene-1-oxide, 3-methyl-1-phenyl-2-phospholene-1-oxide, 1-ethyl-2-phospholene-1-oxide, 3-phospholene isomers of these compounds and so forth are preferred in view of yield and other aspects.

The polycarbodiimide is prepared without solvent or in a non-reactive organic solvent. In the present invention, one of polycarbodiimides prepared as described above or a mixture thereof can be used as the carbodiimide compound, for example. The polycarbodiimide may be partially cross-linked.

Other carbodiimide compounds that can be used for the present invention include, for example, carbodiimide compounds to which hydrophilicity is imparted by adding a polyoxyethylene chain in their molecular structures as described in Japanese Patent Application Laid-open (Kokai) Nos. 63-172718(1988) and 63-264128(1988). Low molecular weight carbodiimide compounds such as monocarbodiimide compounds and dicarbodiimide compounds can also be used for the present invention.

The carbodiimide group of the aforementioned carbodiimide compounds is highly reactive and react with most of active hydrogen groups contained in alcohols, amines, thiols, phenols, carboxylic acids and so forth. For example, reactions with a carboxylic acid, alcohol and amino group proceed as represented by the following formula (I), (II) and (III), respectively (See Frederick Kurzer, K. Douraghi-Zadeh, Chemical Reviews, 67, pp.117–135, (1967) and Andrew Williams, Ibrahim T. Ibrahim, Chemical Reviews, 81, pp.599–606, (1981)).

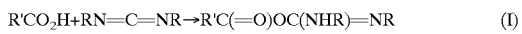

R'CO$_2$H+RN=C=NR→R'C(=O)OC(NHR)=NR    (I)

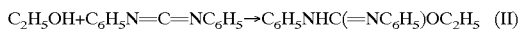

C$_2$H$_5$OH+C$_6$H$_5$N=C=NC$_6$H$_5$→C$_6$H$_5$NHC(=NC$_6$H$_5$)OC$_2$H$_5$    (II)

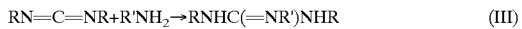

RN=C=NR+R'NH$_2$→RNHC(=NR')NHR    (III)

Therefore, the carrier used for the present invention can securely immobilize nucleic acids through the carbodiimide compounds by utilizing this reactivity of the carbodiimide groups.

(3) Carrier

The carrier of the present invention used for immobilizing nucleic acids comprises the aforementioned base material and the aforementioned carbodiimide compounds carried by the base material. The term "to carry" used in the present specification means that the carbodiimide compounds are not substantially eliminated from the base material in various solvents such as aqueous solvents and organic solvents used when nucleic acids are immobilized on a carrier or the nucleic acid-immobilized substrate is used as a DNA chip or the like.

The aforementioned carbodiimide compounds may be carried by the carrier used for the present invention simply due to physical adhesion or chemically carried through covalent bonds or the like so long as they are carried by the base material. However, the carbodiimide compounds are preferably carried by the base material through covalent bonds on the carrier used for the present invention.

The carbodiimide compounds may be carried by a part or the whole of the base material surface as required.

As the carbodiimide compounds used for preparing a carrier in which the carbodiimide compounds are carried by the base material due to physical adhesion, a polymer compound among the carbodiimide compounds mentioned in the above (2) can be used without any particular limitation. The preferable molecular weight range thereof is from 1000 to 100,000.

Although some polycarbodiimides prepared in the presence of a catalyst promoting carbodiimidation of isocyanate from the organic polyisocyanate compound mentioned in the above (2), for example, have a molecular weight of less than 1000, the molecular weight of such polycarbodiimides can be adjusted to be within the aforementioned range by introducing polyalkylene, polyoxyalkylene, polyurethane, polyamide or the like into both termini of these polycarbodiimides through urea bonds or urethane bonds.

It is preferable for any type of carbodiimide polymer compounds carried by the carrier due to the aforementioned physical adhesion that they have 2 to 100 carbodiimide groups in a molecule. If the carbodiimide polymer compounds have less than two, that is, one carbodiimide group in each molecule, they may lack in the ability to immobilize nucleic acids. To the contrary, if they have 101 or more carbodiimide groups, viscosity may become too high, a solution thereof may not be prepared, and thus their handling property upon immobilization on the base material should be degraded, while they cause no problem concerning the performance for immobilizing nucleic acids.

Such carbodiimide polymer compounds have high adhesion to the aforementioned base material, and they are carried by the base material due to such adhesion. The carbodiimide polymer compounds are carried by the base material due to physical adhesion typically in the form of a coated film.

As a method for providing the carbodiimide polymer compounds on the base material as a coated film, known means such as spraying, dipping, brushing, stamping, vapor deposition and film coating can be employed.

The carrier carrying the carbodiimide compounds through covalent bonds will be described below.

The expression "compound having a carbodiimide group" used in the present specification for the compound having a carbodiimide group carried by the base material surface is defined as a compound independent from the covalent bond moiety present between the compound and the base material surface (that is actually a "group", but a term "compound" is used for convenience). In the present specification, therefore, as for a carrier carrying the compound having a carbodiimide group on the base material through covalent bonds, the compounds having a carbodiimide group are explained as compounds that do not contain a functional group involved in the covalent bond with the base material surface.

The carbodiimide compounds carried through covalent bonds may be of any type of those described in the above (2). Each of the carbodiimide compounds carried by the carrier on the base material surface through a covalent bond preferably has 5 to 30, more preferably 7 to 20 carbodiimide groups in a molecule. If the number of carbodiimide groups in the carbodiimide compound is between 5 and 30, favorable ability to immobilize nucleic acids can be obtained. It is also preferable in its handling because the solution would have appropriate viscosity.

In order to obtain a carrier carrying the compound having a carbodiimide group on the base material surface through covalent bonds (also be referred to as "carbodiimide compound covalently bonded type carrier" hereafter), for example, a carbodiimide compound having a carbodiimide group for immobilizing nucleic acids on the carrier and another functional group to be covalently bonded to the base material surface can be covalently bonded to a functional group of a base material having a functional group that can be covalently bonded with the functional group contained in the carbodiimide compound by an appropriate method.

More specifically, the carbodiimide compound covalently bonded type carrier can be obtained by covalently bonding a compound having two or more carbodiimide groups or having one or more carbodiimide groups and one or more functional groups other than the carbodiimide group to a functional group of a base material having, on its surface, the functional group that can be covalently bonded with one of the aforementioned carbodiimide groups or the aforementioned functional groups other than the carbodiimide group contained in the compound with leaving at least one carbodiimide group free.

As the compound having two or more carbodiimide groups or having one or more carbodiimide groups and one or more functional groups other than the carbodiimide group used to prepare the aforementioned carbodiimide compound covalently bonded type carrier, there can specifically be mentioned compounds having two or more carbodiimide groups or having one or more carbodiimide groups and one or more functional groups other than the carbodiimide group, among the carbodiimide compounds mentioned in the above (2), for example. Further, there can also be used a compound obtained by introducing a functional group to be used for the covalent bond, for example, a functional group selected from a hydroxyl group, an imino group, an amino group, a carboxyl group, an isocyanate group, an isothiocyanate group and so forth into any of the carbodiimide compounds mentioned in the above (2) by an appropriate method to prepare the carbodiimide compound covalently bonded type carrier. In addition, a compound prepared by further introducing a carbodiimide group into any of the carbodiimide compounds mentioned in the above (2) as the functional group to be used for the covalent bond can also be used for the preparation of the carrier. Known conventional methods can be employed as a method of introducing such a functional group into the carbodiimide compound.

As a base material having, on its surface, functional groups that can be covalently bonded with the carbodiimide group or a functional group other than the carbodiimide group contained in the above carbodiimide compounds used for the preparation of the carbodiimide group covalently bonded type carrier, there can be mentioned, for example, the base materials mentioned in the above (1), on which surface functional groups that can form covalent bonds are introduced. The functional group to be introduced is not particularly limited so long as it is a functional group that can be covalently bonded with carbodiimide group or a functional group that can be covalently bonded with the functional group other than the carbodiimide group contained in the aforementioned compound. Specifically, however, a hydroxyl group, an imino group, an amino group, a carboxyl group, a carbodiimide group and so forth can be mentioned. These functional groups are suitably selected depending on the functional group used for the covalent bond contained in the carbodiimide compound, and introduced into the base material surface.

The method for introducing the functional group into the base material surface is suitably selected depending on the material of the base material and the functional group to be introduced. Further, the functional group may be introduced into a part or the whole of the base material surface.

For example, in order to introduce an amino group into the whole surface of a glass base material, the glass base material can be immersed into a solution obtained by dissolving amino-substituted organoalkoxysilane such as 3-aminopropyltriethoxysilane in a suitable solvent, at about 70 to 80° C. for about 2 to 3 hours, taken out from the solution, washed with water and dried by heating at 100 to 120° C. for about 4 to 5 hours.

Introduction of such functional groups onto surfaces of various materials mentioned in the above explanation for the base material has been commonly carried out so far, and methods therefor have been known. Therefore, even when functional groups other than the amino group are introduced into a glass base material or the base material is made of a material other than glass, such functional groups may be introduced onto a surface of the base material by such conventional known methods.

Furthermore, some of plastic base materials among those mentioned in the above (1) have the functional groups mentioned above on the surface. These can be used as they are to prepare the carbodiimide compound covalently bonded type carrier without introducing a functional group into the base material surface. Moreover, a functional group can further be introduced into even such plastic base materials to prepare the carrier.

In order to prepare the carbodiimide compound covalently bonded type carrier used for the present invention, the compound having two or more carbodiimide groups or having one or more carbodiimide groups and one or more functional groups other than the carbodiimide group obtained as described above is reacted with the base material having a functional group that can be covalently bonded with carbodiimide groups or functional groups other than the carbodiimide group on its surface under appropriate conditions so that the functional group on the base material surface should be covalently bonded with the compound with leaving at least one carbodiimide group contained in the compound for each compound free. That is, when each of the compounds has one or more carbodiimide groups and one or more functional groups other than the carbodiimide group, the reaction can be performed under reaction conditions under which the functional group or groups other than the carbodiimide group are used for the covalent bond. When a compound having only carbodiimide groups as functional group is used, the reaction may be performed so that all of the carbodiimide groups should not be used for the covalent bond.

The carrier for immobilizing nucleic acids obtained as described above and comprising a base material and carbodiimide compounds carried by the base material can securely immobilize nucleic acids of various types and sizes by utilizing reactivity of the carbodiimide groups contained in the carbodiimide compounds.

B. Isocyanate Carrier (1) Base Material

A base material used for the carrier for immobilizing nucleic acids according to the present invention plays a role of a support for the carrier and is insoluble in solvents. More specifically, an isocyanate group is introduced onto the surface of the base material used in the present invention as described below to serve as a carrier, and nucleic acids are immobilized thereon. The carrier with the nucleic acids being immobilized thereon is used to produce or analyze nucleic acids. The carrier is substantially insoluble in various solvents such as aqueous solvents and organic solvents used during the procedure of the above production or analysis. The base material used in the present invention is not particularly limited as long as it is insoluble in solvents as described above and basically solid or gel at the ordinary temperature or within the range of the ordinary temperature (0 to 100° C.). Specific examples of the material for the base material of the carrier include plastics, inorganic polymers, metals, natural polymers, and ceramics.

Examples of plastics are polyethylene, polystyrene, polycarbonate, polypropylene, polyamide, phenol resin, epoxy resin, polycarbodiimide resin, poly(vinyl chloride), poly(vinylidene fluoride), poly(ethylene fluoride), polyimide, and acryl resin, etc. Examples of inorganic polymers are glass, quartz, carbon, silica gel, graphite, etc. Examples of metals are those which are solid at the ordinary temperature such as gold, platinum, silver, copper, iron, aluminum, magnet, paramagnet, etc. Examples of natural polymers are cellulose, cellulose derivatives, chitin, chitosan, alginic acid, alginate, etc. Examples of ceramics are apatite, alumina, silica, silicon carbide, silicon nitride, boron carbide, etc.

The above base materials may be in the form of, for example, film, flat plate, particle, molded product (beads, strip, wells of a multiwell plate, tube, mesh, open-cell foam, membrane, paper, needle, fiber, plate, slide, or a cell incubation container), or latex. As a matter of course, its size is not particularly limited.

(2) Production of Carrier

The carrier for immobilizing nucleic acids of the present invention is the above-described base material insoluble in solvents, having an isocyanate group on its surface. This carrier of the present invention can be obtained by, for example, a method to directly introduce an isocyanate group for immobilizing nucleic acids when used as a carrier, onto the surface of the above base material by an appropriate means, a method to allow a film-forming compound having an isocyanate group to be carried by the surface of the above base material by coating or similar means, or a method to allow a compound having an isocyanate group to be carried by the surface of the above base material through a covalent bond.

More specifically, the method of allowing a film-forming compound having an isocyanate group to be carried by the surface of the base material by coating or a similar method is carried out by, for example, dissolving a film-forming compound having an isocyanate group in an appropriate solvent if necessary, coating the resulting solution on the whole or part of the surface of the base material by means of spraying, dipping, brushing, stamp, deposition, film coating, etc., and drying the product if required. Specific examples of the compound having an isocyanate group that can be coated on the surface of the base material by the above method include polycarbodiimide compounds having an isocyanate group at its end, and trialkoxysilane having an isocyanate group such as isocyanate propyltriethoxysilane.

The compound having an isocyanate group can be allowed to be carried by the surface of the base material by, for example, covalently binding a compound having an isocyanate group and the other functional group that is capable of covalently binding to the surface of the base material, to a functional group present on the surface of the base material, which is capable of covalently binding to the above functional group of the compound, by an appropriate method. The carrier of the present invention obtained by allowing a compound having an isocyanate group to be carried by the surface of the base material insoluble in solvents through a covalent bond is excellent in durability since the compound having an isocyanate group is firmly carried by the surface of the base material through a covalent bond.

Furthermore, the method of allowing a compound having an isocyanate group to be carried by the surface of the base material through a covalent bond is exemplified by the production method as described below.

The production method is the method for producing a carrier for immobilizing nucleic acid comprising a base material insoluble in solvents and having an isocyanate group on its surface, wherein said method comprises a step of covalently binding a compound having at least two isocyanate groups, or at least one isocyanate group and at least one functional group other than the isocyanate group, or at least one isocyanate group and a halogen atom (hereinafter sometimes simply referred to as "isocyanate compound") onto a functional group on the surface of the base material insoluble in solvents, which is capable of covalently binding to the isocyanate group or to the functional group other than the isocyanate group or the halogen atom with leaving at least one isocyanate group of the compound free.

Examples of the compound having at least two isocyanate groups in its molecule used in the production method include hexamethylenediisocyanate, toluenediisocyanate, tetramethylxylenediisocyanate, naphthalenediisocyanate, etc.

Examples of the functional group other than the isocyanate group of the compound having at least one isocyanate group and at least one functional group other than the isocyanate group, or at least one isocyanate group and a halogen atom in its molecule include a hydroxyl group, an amino group, an imino group, a carboxyl group, etc. Such an isocyanate compound is exemplified by chloromethyl isocyanate, chloroethyl isocyanate, etc.

The base material insoluble in solvents used in the production method, which has, on its surface, a functional group capable of covalently binding to an isocyanate group, or a functional group other than the isocyanate group or a halogen atom of the above compound, includes those insoluble in solvents described in <1>B(1) on the surface of which a functional group capable of covalently binding to the above-described groups is introduced. The functional group to be introduced is not particularly limited as long as it is capable of covalently binding to an isocyanate group, or a functional group other than the isocyanate group or a halogen atom of the above compound. Specific examples thereof include a hydroxyl group, an imino group, an amino group, a carboxyl group, etc. These functional groups are appropriately selected depending on the functional group of the above isocyanate compound and bound to the surface of the base material.

The method for introducing the above-described functional groups on the surface of the base material insoluble in solvents is appropriately selected depending on the material of the base material or the functional groups to be introduced. The functional groups can be introduced on the whole or part of the surface of the base material.

For example, an amino group can be introduced onto the whole of the surface of the glass base material by dissolving amino-substituted organoalkoxysilane such as 3-aminopropyltriethoxysilane in an appropriate solvent, dipping a glass base material in the resulting solution at about 70 to 80° C. for about 2 to 3 hours, taking the base material out of the solution to wash it with water, and heat-drying it at about 100 to 120° C. for about 4 to 5 hours.

A functional group other than an amino group can be introduced onto the glass base material, or an amino group can be introduced onto the base material made of the material other than glass by a known method conventionally used for introducing various functional groups onto the surface of various materials as listed in the above description of the base material.

Some plastic base materials among the base materials listed in <1>B(1) have the above functional groups on their surface originally. In this case, such base materials can be used as they are without introducing the functional groups on their surface. It is also possible to introduce the functional groups to such plastic base materials to be used in the present invention.

In the production method, a compound having at least two isocyanate groups, or at least one isocyanate group and at least one functional group other than the isocyanate group, or at least one isocyanate group and a halogen atom is reacted with the base material insoluble in solvents, which has, on its surface, a functional group capable of covalently binding to an isocyanate group, or the above-described functional group other than the isocyanate group or a halogen atom, under appropriate conditions to covalently bind the above compound to the above functional group on the surface of the base material with leaving at least one isocyanate group of the above compound free. In other words, when the compound has at least one isocyanate group and at least one functional group other than the isocyanate group or at least one isocyanate group and a halogen atom, the reaction is carried out under such conditions that the functional group other than the isocyanate group or the halogen atom is subjected to the covalent bonding. When the compound having only an isocyanate group as a functional group is used, the reaction is carried out under such conditions that all of the isocyanate groups are not subjected to the covalent bonding.

The thus-obtained carrier for immobilizing nucleic acids according to the present invention comprising a base material insoluble in solvents and having an isocyanate group on its surface can be used to immobilize various nucleic acids utilizing the reactivity of the isocyanate group. The isocyanate group is reactive, for example, with a hydroxyl group as shown in the following formula (III) and with an amino group as shown in the following formula (IV).

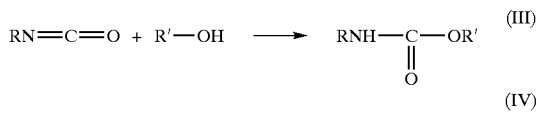

(2) Nucleic Acid-immobilized Substrate

In the nucleic acid-immobilized substrate of the present invention, the same kind or different kinds of nucleic acids are immobilized in the form of dots on a plurality of sites through the carbodiimide group or the isocyanate group on a carrier comprising the aforementioned base material and the carbodiimide compound or the isocyanate compound carried by the base material.

The expression "nucleic acids are immobilized in the form of dots on a carrier" in the nucleic acid-immobilized substrate of the present invention means that the site where nucleic acid are immobilized are sufficiently small so that a plurality of such sites can be provided on the carrier. The shape of the aforementioned dots is not particularly limited and suitably selected depending on the method for use, applications and so forth of the nucleic acid-immobilized substrate.

Specifically, each of the aforementioned dots on which nucleic acids are immobilized in the nucleic acid-immobilized substrate of the present invention may be in a substantially circular shape and have a diameter of from 10 to 3000 $\mu$m. The preferred size of the dots is about 50 to 2000 $\mu$m in diameter, more preferably about 100 to 1500 $\mu$m in diameter. The substantially circular shape is not limited to a circle, but includes any shapes is near a circle such as ellipse or the like without any particular limitation. For example, the diameter of an ellipse is represented as the average value of its long diameter and short diameter.

If the diameter of the dots is less than 10 $\mu$m, detection may become difficult. If the diameter exceeds 3000 $\mu$m, it may become difficult to secure an appropriate number of dots per unit area. Therefore, it is preferable to use a size of the dots within the above range in order to make detection easy and secure a required number of dots per unit area.

The number of sites where nucleic acids are immobilized in the form of dots on the nucleic acid-immobilized substrate of the present invention is not particularly limited, and suitably selected depending on the method of use, applications and so forth of the nucleic acid-immobilized substrate. Specifically, however, it is preferable that the number of sites where the nucleic acids are immobilized is about 10 to 10000, more preferably about 50 to 350, per cm$^2$ on the base material. Further, the positions of the sites where nucleic acids are immobilized in the form of dots on the nucleic acid-immobilized substrate of the present invention are also selected as required depending on the method of use, applications and so forth of the nucleic acid-immobilized substrate.

As nucleic acids immobilized on the nucleic acid-immobilized substrate of the present invention, there can be mentioned natural or synthesized DNA (including oligonucleotides) or RNA (including oligonucleotides) without particular limitation. In the present invention, nucleic acids having a chain length of 10 to 300 nucleotides, in particular, which have conventionally been difficult to be immobilized, can be immobilized. Further, nucleic acids to be immobilized may be single-stranded or double-stranded. Furthermore, in the present invention, nucleic acids having functional groups that are reactive with a carbodiimide group or an isocyanate group are usually used as the aforementioned nucleic acids. In the nucleic acid-immobilized substrate of the present invention, nucleic acids immobilized in the form of dots may be of the same kind or different kinds. If different kinds of nucleic acids are used, the positional arrangement of nucleic acids of each kind and so forth may be selected as required depending on the method of use, applications and so forth of the obtained nucleic acid-immobilized substrate.

In order to immobilize such nucleic acids on the aforementioned carrier in the form of dots, nucleic acids can be brought into contact and reacted with the carbodiimide compound or the isocyanate compound by providing a small amount of the nucleic acids in the form of dots in a required size on the sites of the carrier where the carbodiimide compound or the isocyanate compound is carried, under appropriate conditions. Through the reaction of the carbodiimide group of the carbodiimide compound or the isocyanate group of the isocyanate compound carried by the carrier with hydroxyl groups, amino groups, thiol groups, carboxyl groups and so forth contained in the nucleic acids, the nucleic acids are covalently bonded with the carbodiimide compound or the isocyanate compound. As a result, the nucleic acids are immobilized on the carrier.

Specifically, nucleic acids contained in water or a buffer are usually provided so that activity of the nucleic acids to be immobilized is maintained in their reaction of the both substances upon contact. The temperature during the reaction upon contact is preferably 0 to 100° C. in general so that activity of the nucleic acids should not be degraded.

In the present invention, as means for providing a small amount of nucleic acids, usually provided as water or a buffer containing nucleic acids, on the carrier in the form of dots, methods using a dispenser, pin, bubble jet or the like may be employed, but the present invention is not limited to these methods. Apparatuses for providing a small amount of solution by these methods are commercially available and they can be used for the present invention.

When the nucleic acid-immobilized substrate of the present invention is used for an analysis or the like, nucleic acids other than the aforementioned immobilized nucleic acids are often brought into contact with it. In order to prevent such nucleic acids or the like other than the immobilized nucleic acids from nonspecifically binding with an unreacted carbodiimide group contained in the carbodiimide compound or an unreacted isocyanate group contained in the isocyanate compound carried by the carrier, an excess amount of bovine serum albumin (BSA), casein, nucleic acids generally used in hybridization reactions for blocking such as salmon sperm DNA or the like is preferably brought into contact with the carrier to block a free carbodiimide group or a free isocyanate group after nucleic acids are immobilized in the form of dots on the carrier as described above.

In the nucleic acid-immobilized substrate of the present invention obtained as described above, the nucleic acids are very securely carried by the carrier and are not dropped even by the washing methods widely employed for hybridization or the like (washing methods using a surfactant). Therefore, when an analysis or the like is performed by using this, the analysis is enabled with excellent reproducibility and quantification characteristics. In addition, since nucleic acids can be immobilized on the nucleic acid-immobilized substrate of the present invention without limitation on the number of chains or length, various nucleic acids can simultaneously be handled on the same base material. Thus, it can be said that the nucleic acid-immobilized substrate of the present invention can be used as a DNA array or the like with excellent performance in techniques for determining nucleotide sequences by hybridization using a number of nucleic acids such as sequencing by hybridization (SBH) and sequencing by hybridization with oligonucleotide matrix (SHOM).

EXAMPLES

The present invention will be explained more specifically with reference to the following examples. Unless otherwise noted, "%" means % by weight.

Preparation Example 1

Preparation of Carbodiimidated Slide Glass
(1) Preparation of Carbodiimide Compound Solution 117.9 g of 4,4'-dicyclohexylmethane diisocyanate and 12.5 g of cyclohexyl isocyanate were allowed to react in the presence of 1.3 g of a carbodiimidation catalyst (3-methyl-1-phenyl-2-phospholene-1-oxide) under nitrogen atmosphere at 180° C. for 4 days. A carbodiimide compound (polymerization degree: 10, number average molecular weight: 2400) was obtained as powder at room temperature. 10 g of this compound was dissolved in 200 ml of dichloromethane to obtain a carbodiimide compound solution.

(2) Preparation of Aminated Slide Glass

To 180 ml of distilled water, 20 ml of 10% (v/v) solution of 3-aminopropyltriethoxysilane in ethanol was added and the mixture was stirred sufficiently. After the pH was adjusted to 3 to 4 by adding 6 N HCl thereto, 15 pieces of slide glass were immersed in the solution and treated at 75° C. for 2 hours by heating. After the heat treatment, the slide glass pieces were taken out from the solution, sufficiently rinsed with distilled water, and then dried at 115° C. for 4 hours by heating to obtain aminated slide glass.

(3) Preparation of Carbodiimidated Slide Glass 15 pieces of the aminated slide glass obtained in (2) were immersed in 200 ml of the carbodiimide compound solution obtained in (1), immediately taken out from it, and then dried at 60° C. for 1 hour by heating. Subsequently, these slide glass pieces were washed twice with 200 ml of dichloromethane for 10 minutes for each washing and dried at 40° C. for 2 hours to obtain carbodiimidated slide glass.

Preparation Example 2

Preparation of Isocyanated Slide Glass
(1) Preparation of Aminated Slide Glass

A solution of 10% (v/v) 3-aminopropyl-triethoxysilane in ethanol (20 ml) was added to 180 ml of distilled water, and the mixture was stirred well. After the pH was adjusted to 3 to 4 by adding 6 N HCl thereto, 15 pieces of slide glasses were dipped in the solution and treated under heating at 75° C. for 2 hours. After completion of the heat treatment, slide glass pieces were taken out from the solution, washed well with distilled water, and dried by heating 115° C. for 4 hours to obtain aminated slide glass.

(2) Preparation of Isocyanated Slide Glasses

Fifteen pieces of the aminated slide glasses obtained above were dipped in a 2.5% solution of hexamethylenediisocyanate in chloroform and immediately taken out. The slide glass pieces were washed twice with 200 ml of chloroform for 10 minutes and dried at 40° C. for 2 hours to obtain isocyanated slide glass.

Example 1
(1) Immobilization of Nucleic Acids Onto Carbodiimidated Slide Glass

By polymerase chain reaction (PCR) using chromosomal DNA of *Escherichia coli* O-157 as a template and oligonucleotides having the nucleotide sequences shown by SEQ ID NOS: 1 and 2 as primers, a vero toxin gene (VT2 gene) fragment having the nucleotide sequence shown by SEQ ID NO: 3 was amplified.

The above amplification product was dissolved in 2 M NaCl to obtain a DNA solution of 0.1 pmol/μl. By using SPBIO (arrayer, Hitachi Software Engineering), the DNA solution was spotted on predetermined 500 sites with a diameter of 200 μm on the carbodiimidated slide glass obtained in the above Preparation Example 1. The carbodiimidated slide glass on which DNA was spotted was placed in a drier and dried at 37° C. for 15 minutes. Subsequently, it was immersed in Buffer A (0.2 M sodium chloride, 0.1 M Tris/HCl (pH 7.5), 0.05% Triton X-100) containing 3% bovine serum albumin (BSA) and then dried at 37° C. for 15 minutes. Then, the slide glass was washed with TE buffer (10 mM Tris/HCl, pH 7.2, 1 mM EDTA) and dried at 37° C. for 15 minutes to obtain carbodiimidated slide glass on which nucleic acids (double-stranded DNA) were immobilized.

(2) Hybridization

The carbodiimidated slide glass on which DNA was immobilized was immersed in hot water at 100° C. for 10 minutes, and then in ice cooled water for 5 minutes to denature the double-stranded DNA. 30 μl of a hybridization solution was placed on a portion of this slide glass on which DNA was immobilized, and the slide glass was covered with parafilm and incubated overnight on a water bath at 42° C. The composition of the hybridization solution is mentioned below. A biotinylated probe was prepared by amplifying the VT2 gene by using the aforementioned oligonucleotide primers. It was thermally denatured to be used as a probe.

[Composition of Hybridization Solution]

5×SSC (SSC: 1.5 M NaCl, 0.15 M sodium citrate)

1×Denhardt's solution (100 mg of Ficoll, 100 mg of polyvinylpyrrolidone, 100 mg of bovine serum albumin, and $H_2O$ to 500 ml)

25 mM sodium phosphate buffer (containing $Na_2HPO_4$ and $NaH_2PO_4$), pH 6.5

45% formamide 10 ng/ml of sonicated salmon sperm DNA 2 pmol of biotinylated probe (3) Posthybridization Washing After the hybridization, the parafilm was removed from the slide glass. The hybridization solution was slightly sucked and the posthybridization washing was performed under the following conditions to remove the nonspecifically adsorbed probe.

[Posthybridization Washing Solution and Conditions]

Stage 1: 2×SSC, 1% SDS; room temperature, 5 minutes, twice

Stage 2: 0.2×SSC, 1% SDS; 40° C., 5 minutes, twice

Stage 3: 2×SSC; room temperature, 5 minutes, once (4) Detection of Hybridization The slide glass after the above posthybridization washing was immersed in 50 ml of Buffer A containing 3% BSA to perform blocking at room temperature for 30 minutes. Then, the slide glass was immersed in 20 ml of streptavidin-alkaline phosphatase conjugate solution (Gibco BRL, stock solution was diluted 1000 times with Buffer A containing 3% BSA) and allowed to react at room temperature for 30 minutes. Subsequently, the slide glass was immersed in 50 ml of Buffer A, and left at room temperature for 5 minutes. This procedure was repeated twice to remove the conjugates that were not bound to biotin.

Subsequently, the slide glass was washed once with 30 ml of Buffer B (0.1 M sodium chloride, 0.1 M Tris/HCl, pH 9.5, 50 mM magnesium chloride). Finally, the slide glass was immersed in a substrate solution (30 ml of Buffer B+25 μl of BCIP solution (50 mg of 5-bromo-4-chloro-3-indolylphosphate in 900 ml of dimethylformamide)+50 μl of NBT solution (50 mg of nitroblue tetrazolium in 1.8 ml of 70% ethanol)) and left at room temperature for 3 hours. As a result of the color development reaction, hybridization signals were obtained at the positions on the slide glass where DNA was immobilized.

Example 2

(1) Immobilization of Nucleic Acids Onto Carbodiimidated Slide Glass

λDNA of about 48 kb was dissolved in 0.1 M $MgCl_2$ to obtain a DNA solution of 100 ng/μl. By using SPBIO (arrayer, Hitachi Software Engineering), the DNA solution was spotted on predetermined 500 sites with a diameter of 200 μm on the carbodiimidated slide glass obtained in the above Preparation Example 1. The carbodiimidated slide glass on which DNA was spotted was placed in a drier and dried at 37° C. for 15 minutes. Subsequently, it was immersed in Buffer A containing 3% BSA and then dried at 37° C. for 15 minutes. Then, the slide glass was washed with TE buffer and dried at 37° C. for 15 minutes to obtain carbodiimidated slide glass on which nucleic acids (DNA) were immobilized.

(2) Hybridization

The carbodiimidated slide glass on which DNA was immobilized was immersed in hot water at 100° C. for 10 minutes and in ice cooled water for 5 minutes to denature the double-stranded DNA. 50 μl of a hybridization solution was placed on each of the portions of the slide glass on which DNA was immobilized, and the slide glass was covered with parafilm and incubated overnight on a water bath at 42° C. The composition of the hybridization solution is mentioned below. The biotinylated probe was prepared by biotinylating λDNA digested with EcoRI by using Carbobiotin (Nisshinbo Industries).

[Composition of Hybridization Solution]

5×SSC (SSC: 1.5 M NaCl, 0.15 M sodium citrate)

1×Denhardt's solution

10% dextran

45% formamide 10 ng/ml of sonicated salmon sperm DNA 1 pmol of biotinylated probe (3) Posthybridization Washing After the hybridization, the parafilm was removed from the slide glass. The hybridization solution was slightly sucked and the posthybridization washing was performed under the following conditions to remove the nonspecifically adsorbed probe.

[Posthybridization Washing Conditions]

Stage 1: 2×SSC, 1% SDS; room temperature, 5 minutes, twice

Stage 2: 0.2×SSC, 1% SDS; 48° C., 5 minutes, twice

Stage 3: 2×SSC; room temperature, 5 minutes, once (4) Detection of Hybridization The slide glass after the above posthybridization washing was immersed in 50 ml of Buffer A containing 3% BSA and the blocking was performed at room temperature for 30 minutes. Then, the slide glass was immersed in 45 ml of streptavidin-alkaline phosphatase conjugate solution (stock solution was diluted 2000 times with Buffer A containing 3% BSA) and allowed to react at room temperature for 30 minutes. Subsequently, the slide glass was immersed in 50 ml of Buffer A at room temperature for 5 minutes. This procedure was repeated twice to remove conjugates that were not bound to biotin.

Subsequently, the slide glass was washed once with 30 ml of Buffer B. Finally, the slide glass is immersed in a substrate solution (20 ml of Buffer B+18 μl of BCIP solution+50 μl of NBT solution) and left at room temperature for 3 hours. As a result of the color development reaction, hybridization signals were obtained at the positions on the slide glass where DNA was immobilized.

Example 3

(1) Immobilization of Nucleic Acids Onto Carbodiimidated Slide Glass

An oligonucleotide (21-mer) having the nucleotide sequence shown by SEQ ID NO: 2 was dissolved in 2 M NaCl to obtain a DNA solution of 100 ng/μl. By using SPBIO (arrayer, Hitachi Software Engineering), the DNA solution was spotted on predetermined 500 sites with a diameter of 200 μm on the carbodiimidated slide glass obtained in the above Preparation Example 1. AS control, a solution of DNA (tet) not complementary to the probe at 100 ng/μl was spotted on predetermined 100 sites on the carbodiimidated slide glass. The carbodiimidated slide glass on which DNA was spotted was placed in a drier and dried at 37° C. for 15 minutes. Subsequently, it was immersed in Buffer A containing 3% BSA and then dried at 37° C. for 15 minutes. Then, the slide glass was washed with TE buffer and dried at 37° C. for 15 minutes to obtain carbodiimidated slide glass on which nucleic acids (single-stranded DNA) were immobilized.

(2) Hybridization

50 μl of a hybridization solution was placed on portions of the slide glass on which DNA was immobilized, and the slide glass was covered with parafilm and incubated overnight on a water bath at 42° C. The composition of the hybridization solution is mentioned below. The the same biotinylated probe as used in Example 1 was used as the probe.

[Composition of Hybridization Solution]

3×SSC

10% dextran 1 pmol of biotinylated probe (3) Posthybridization Washing

After the hybridization, the parafilm was removed from the slide glass. The hybridization solution was slightly sucked and the posthybridization washing was performed under the following conditions to remove the nonspecifically adsorbed probe.

[Posthybridization Washing Conditions]

Stage 1: 2×SSC, 0.1% SDS; room temperature, 5 minutes, twice

Stage 2: 0.2×SSC, 0.1% SDS; 40° C., 5 minutes, twice

Stage 3: 2×SSC; room temperature, 5 minutes, once (4) Detection of Hybridization The slide glass was immersed in 50 ml of Buffer A containing 3% BSA to perform blocking at room temperature for 30 minutes. Then, the slide glass was immersed in 45 ml of streptavidin-alkaline phosphatase conjugate solution (stock solution was diluted 2000 times with Buffer A containing 3% BSA) and allowed to react at room temperature for 30 minutes. Subsequently, the slide glass was immersed in 50 ml of Buffer A and left at room temperature for 5 minutes. This procedure was repeated twice to remove the conjugates that were not bound to biotin. Subsequently, the slide glass was washed once with 30 ml of Buffer B. Finally, the slide glass was immersed in a substrate solution (20 ml of Buffer B+18 μl of BCIP solution+36 μl of NBT solution) and left at room temperature for 3 hours. As a result of the color development reaction, hybridization signals were obtained only at the positions on the slide glass where the oligonucleotide having the nucleotide sequence shown by SEQ ID NO: 2 was immobilized, whereas no hybridization signal was detected at the positions where tet was immobilized.

Example 4

(1) Immobilization of Nucleic Acids Onto Carbodiimidated Slide Glass

The oligonucleotide (21-mer) having the nucleotide sequence shown by SEQ ID NO: 2 was dissolved in 2 M NaCl to obtain a DNA solution of 100 ng/µl. By using SPBIO (arrayer, Hitachi Software Engineering), the DNA solution was spotted on predetermined 500 sites with a diameter of 200 µm on the carbodiimidated slide glass obtained in the above Preparation Example 1. As control, a solution of DNA (tet) not complementary to the probe was spotted on predetermined 100 sites on the slide glass. The carbodiimidated slide glass on which DNA was spotted was placed in a drier and dried at 37° C. for 15 minutes. Subsequently, it was immersed in Buffer A containing 3% BSA and then dried at 37° C. for 15 minutes. Then, the slide glass was washed with TE buffer and dried at 37° C. for 15 minutes to obtain carbodiimidated slide glass on which nucleic acids (single-stranded DNA) were immobilized.

(2) Hybridization

50 µl of a hybridization solution was placed on each of the portions on the slide glass on which DNA was immobilized, and the slide glass was covered with parafilm and incubated overnight on a water bath at 42° C. The composition of the hybridization solution is mentioned below. The same biotinylated probe as used in Example 1 was used as the probe.

[Composition of Hybridization Solution]

3×SSC

10% dextran 1 pmol of biotinylated probe (3) Posthybridization Washing

After the hybridization, the parafilm was removed from the slide glass. The hybridization solution was slightly sucked and the posthybridization washing was performed under the following conditions to remove the nonspecifically adsorbed probe.

[Posthybridization Washing Solution and Conditions]

Stage 1: 2×SSC, 0.1% SDS; room temperature, 5 minutes, twice

Stage 2: 0.2×SSC, 0.1% SDS; 40° C., 5 minutes, twice

Stage 3: 2×SSC; room temperature, 5 minutes, once (4) Detection of Hybridization The slide glass was immersed in 50 ml of Buffer A containing 3% BSA to perform blocking at room temperature for 30 minutes. Then, the slide glass was immersed in 45 ml of streptavidin-alkaline phosphatase conjugate solution (stock solution was diluted 2000 times with Buffer A containing 3% BSA) and allowed to react at room temperature for 30 minutes. Subsequently, the slide glass was immersed in 50 ml of Buffer A and left at room temperature for 5 minutes. This procedure was repeated twice to remove conjugates that were not bound to biotin. Subsequently, the slide glass was washed once with 30 ml of Buffer B. Finally, the slide glass was immersed in a substrate solution (20 ml of Buffer B+18 µl of BCIP solution+36 µl of NBT solution) and left at room temperature for 3 hours. As a result of the color development reaction, hybridization signals were obtained only at the positions on the slide glass where the oligonucleotide having the nucleotide sequence shown by SEQ ID NO: 2 was immobilized, whereas no hybridization signal was detected at the positions where tet was immobilized.

Example 5

(1) Immobilization of Nucleic Acids Onto Carbodiimidated Slide Glass

By polymerase chain reaction (PCR) using chromosomal DNA of Escherichia coli O-157 as a template and oligonucleotides having the nucleotide sequences shown by SEQ ID NOS: 1 and 4 as primers, a vero toxin gene (VT2 gene) fragment having the nucleotide sequence shown by SEQ ID NO: 5 was amplified.

The above amplification product was dissolved in 2 M NaCl to obtain a DNA solution of 0.1 pmol/µl. By using SPBIO (arrayer, Hitachi Software Engineering), the DNA solution was spotted on predetermined 1000 sites with a diameter of 200 µm on the carbodiimidated slide glass obtained in the above Preparation Example 1. The carbodiimidated slide glass on which DNA was spotted was placed in a drier and dried at 37° C. for 15 minutes. Subsequently, it was immersed in Buffer A containing 3% BSA and then dried at 37° C. for 15 minutes. Then, the slide glass was washed with TE buffer and dried at 37° C. for 15 minutes to obtain carbodiimidated slide glass on which nucleic acids (double-stranded DNA) were immobilized.

(2) Hybridization

The carbodiimidated slide glass on which DNA was immobilized was immersed in hot water at 100° C. for 10 minutes and then in ice cooled water for 5 minutes to denature the double-stranded DNA. 30 µl of a hybridization solution was placed on each of portions of the slide glass on which DNA was immobilized, and the slide glass was covered with parafilm and incubated overnight on a water bath at 42° C. The composition of the hybridization solution is mentioned below. The biotinylated probe was prepared by amplifying the VT2 gene by using the aforementioned oligonucleotide primers. The product was thermally denatured to be used as the probe.

[Composition of Hybridization Solution]

5×SSC (SSC: 1.5 M NaCl, 0.15 M sodium citrate)

1×Denhardt's solution 25 mM sodium phosphate buffer (containing $Na_2HPO_4$ and $NaH_2PO_4$), pH 6.5

45% formamide 10 ng/ml of sonicated salmon sperm DNA 2 pmol of biotinylated probe (3) Posthybridization Washing After the hybridization, the parafilm was removed from the slide glass. The hybridization solution was slightly sucked and the posthybridization washing was performed under the following conditions to remove the nonspecifically adsorbed probe.

[Posthybridization Washing solution and Conditions]

Stage 1: 2×SSC, 1% SDS; room temperature, 5 minutes, twice

Stage 2: 0.2×SSC, 1% SDS; 40° C., 5 minutes, twice

Stage 3: 2×SSC; room temperature, 5 minutes, once (4) Detection of Hybridization The slide glass after the above posthybridization washing was immersed in 50 ml of Buffer A containing 3% BSA to perform blocking at room temperature for 30 minutes. Then, the slide glass was immersed in 20 ml of streptavidin-alkaline phosphatase conjugate solution (Gibco BRL, stock solution was diluted 1000 times with Buffer A containing 3% BSA) and allowed to react at room temperature for 30 minutes. Subsequently, the slide glass was immersed in 50 ml of Buffer A and left at room temperature for 5 minutes.

This procedure was repeated twice to remove conjugates that were not bound to biotin.

Subsequently, the slide glass was washed once with 30 ml of Buffer B. Finally, the slide glass was immersed in a substrate solution (30 ml of Buffer B+25 µl of BCIP solution+50 µl of NBT solution) and left at room temperature for 3 hours. As a result of the color development reaction, hybridization signals were obtained at the positions on the slide glass where DNA was immobilized.

Example 6

Isocyanated slide glass on which nucleic acids were immobilized was obtained in a similar manner as Example 1(1) except that the isocyanated slide glass obtained in the above Preparation Example 2 was used instead of the carbodiimidated slide glass in Example Example 7

Isocyanated slide glass on which nucleic acids were immobilized was obtained in a similar manner as Example 2(1) except that the isocyanated slide glass obtained in the above Preparation Example 2 was used instead of the carbodiimidated slide glass in Example 2(1).

Example 8

Isocyanated slide glass on which nucleic acids were immobilized was obtained in a similar manner as Example 3(1) except that the isocyanated slide glass obtained in the above Preparation Example 2 was used instead of the carbodiimidated slide glass in Example 3(1).

Example 9

Carbodiimidated slide glass on which nucleic acids were immobilized was obtained in a similar manner as Example 1(1) except that the carbodiimidated slide glass was irradiated with ultraviolet light (254 nm) at 120 mJ/cm$^2$ instead of the steps of placing the carbodiimidated slide glass in a drier and drying it at 37° C. for 15 minutes in Example 1(1).

Example 10

Isocyanated slide glass on which nucleic acids were immobilized was obtained in a similar manner as Example 6 except that the isocyanated slide glass was irradiated with ultraviolet light (254 nm) at 120 mJ/cm$^2$ instead of the steps of placing the isocyanated slide glass in a drier and drying it at 37° C. for 15 minutes in Example 6.

Comparative Example 1

(1) Immobilization of Nucleic Acids Onto Poly-L-lysine-coated Slide Glass

The oligonucleotide (21-mer) having the nucleotide sequence shown by SEQ ID NO: 2 was dissolved in 0.2× SSC to obtain a DNA solution of 100 ng/µl. By using SPBIO (arrayer, Hitachi Software Engineering), the DNA solution was spotted on predetermined 500 sites with a diameter of 200 µm on a poly-L-lysine-coated slide glass (Sigma). As control, a solution of DNA (tet) not complementary to the probe was spotted on 100 sites. The poly-L-lysine-coated slide glass on which DNA was spotted was placed in a chamber, allowed to react at room temperature for 2 hours, and dried in a drier at 80° C. under reduced pressure for 2 hours. Then, the slide glass was washed with 0.1% SDS and immersed in a blocking solution (1 g of succinic anhydride, 100 ml of N-methyl-pyrrolidone and 100 ml of 0.2 M sodium borate, pH 8.0) at room temperature for 10 minutes, then washed 4 times with distilled water to obtain poly-L-lysine-coated slide glass on which nucleic acids were immobilized.

(2) Hybridization

50 µl of a hybridization solution was placed on each of portions of the poly-L-lysine-coated slide glass on which DNA was immobilized, and the slide glass was covered with parafilm and incubated overnight on a water bath at 42° C. The composition of the hybridization solution is mentioned below. The same biotinylated probe as used in Example 1 was used as the probe.

[Composition of Hybridization Solution]

3×SSC

10% dextran 1 pmol of biotinylated probe (3) Posthybridization Washing

After the hybridization, the parafilm was removed from the slide glass. The hybridization solution was slightly sucked and the posthybridization washing was performed under the following conditions to remove the nonspecifically adsorbed probe.

[Posthybridization Washing Conditions]

Stage 1: 2×SSC, 0.1% SDS; room temperature, 5 minutes, twice

Stage 2: 0.2×SSC, 0.1% SDS; 40° C., 5 minutes, twice

Stage 3: 2×SSC; room temperature, 5 minutes, once (4) Detection of Hybridization The slide glass was immersed in 50 ml of Buffer A containing 3% BSA to perform blocking at room temperature for 30 minutes. Then, the slide glass was immersed in 45 ml of a streptavidin-alkaline phosphatase conjugate solution (stock solution was diluted 2000 times with Buffer A containing 3% BSA) and allowed to react at room temperature for 30 minutes. Subsequently, the slide glass was immersed in 50 ml of Buffer A and left at room temperature for 5 minutes. This procedure was repeated twice to remove the conjugates that were not bound to biotin. Subsequently, the slide glass was washed once with 30 ml of Buffer B. Finally, the slide glass was immersed in a substrate solution (20 ml of Buffer B+18 µl of BCIP solution+36 µl of NBT solution) and left at room temperature for 3 hours to cause the color development reaction. As a result, no hybridization signal was obtained.

Comparative Example 2

(1) Immobilization of Nucleic Acids Onto Poly-L-lysine-coated Slide Glass

The oligonucleotide (21-mer) having the nucleotide sequence shown by SEQ ID NO: 2 was dissolved in 0.2× SSC to obtain a DNA solution of 100 ng/µl. By using SPBIO (arrayer, Hitachi Software Engineering), the DNA solution was spotted on predetermined 500 sites with a diameter of 200 µm on a poly-L-lysine-coated slide glass (Sigma). As control, a solution of DNA (tet) not complementary to the probe was spotted on 100 sites. The poly-L-lysine-coated slide glass on which DNA was spotted was placed in a chamber, allowed to react at room temperature for 2 hours, and dried in a drier at 80° C. under reduced pressure for 2 hours. Then, the slide glass was washed with 0.1% SDS and immersed in a blocking solution (1 g of succinic anhydride, 100 ml of N-methyl-pyrrolidone and 100 ml of 0.2 M sodium borate, pH 8.0) at room temperature for 10 minutes, then washed 4 times with distilled water to obtain poly-L-lysine-coated slide glass on which nucleic acids were immobilized.

(2) Hybridization

50 μl of a hybridization solution was placed on each of portions of the poly-L-lysine-coated slide glass on which DNA was immobilized, and the slide glass was covered with parafilm and incubated overnight on a water bath at 42° C. The composition of the hybridization solution is mentioned below. The same biotinylated probe as used in Example 1 was used as a probe.

[Composition of Hybridization Solution]

3×SSC,

10% dextran 1 pmol of biotinylated primer (3) Post Hybridization Washing

After the hybridization, parafilm was removed from the slide glass. The hybridization solution was slightly sucked and the posthybridization washing was performed under the following conditions to remove the nonspecifically adsorbed probe.

[Posthybridization Washing Conditions]

Stage 1: 2×SSC, 0.1% SDS; room temperature, 5 minutes, twice

Stage 2: 0.2×SSC, 0.1% SDS; 40° C., 5 minutes, twice

Stage 3: 2×SSC; room temperature, 5 minutes, once (4) Detection

The slide glass was immersed in 50 ml of Buffer A containing 3% BSA to perform blocking at room temperature for 30 minutes. Then, the slide glass was immersed in 45 ml of a streptavidin-alkaline phosphatase conjugate solution (stock solution was diluted 2000 times with Buffer A containing 3% BSA) and allowed to react at room temperature for 30 minutes. Subsequently, the slide glass was immersed in 50 ml of Buffer A and left at room temperature for 5 minutes. This procedure was repeated twice to remove conjugates that were not bound to biotin. Subsequently, the slide glass was washed once with 30 ml of Buffer B. Finally, the slide glass was immersed in a substrate solution (20 ml of Buffer B+18 μl of BCIP solution+36 μl of NBT solution) and left at room temperature for 3 hours to cause the color development reaction. As a result, no hybridization signal was obtained.

What is claimed is:

1. A nucleic acid-immobilized substrate which comprises a carrier comprising an aminated support and a compound having a carbodiimide group carried by the support, and the same kind or different kinds of nucleic acids immobilized in the form of dots through the carbodiimide group at a plurality of sites on the carrier, said compound having the carbodiimide group is carried on a surface of the support through a covalent bond.

2. The nucleic acid-immobilized substrate according to claim 1, wherein the dots each have a substantially circular shape and a diameter of from 10 to 3000 μm.

3. The nucleic acid-immobilized substrate according to claim 1, wherein the nucleic acids have a chain length of from 10 to 300 nucleotides.

4. The nucleic acid-immobilized substrate according to claim 1, wherein number of the dots in which nucleic acids are immobilized is 10 to 10,000 per $cm^2$ of the substrate.

* * * * *

SEQUENCE LISTING

<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: primer for
      PCR

<400> SEQUENCE: 1
aaatgggtac tgtgcctgtt a                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: primer for
      PCR

<400> SEQUENCE: 2
gttacccaca taccacgaat c                                              21

<210> SEQ ID NO 3
<211> LENGTH: 1254
<212> TYPE: DNA
<213> ORGANISM: Escherichia coli

<400> SEQUENCE: 3
aaatgggtac tgtgcctgtt actgggtttt ccttcggtat cctattcccg ggagtttatg      60
atagactttt cgacccaaca aagttatgtc tcttcgttaa atagtatacg gacagagata     120
tcgacccctc ttgaacatat atctcagggg accacatcgg tgtctgttat taaccacacc     180
ccaccgggca gttattttgc tgtggatata cgagggcttg atgtctatca ggcgcgtttt     240
gaccatcttc gtctgattat tgagcaaaat aatttatatg tggctgggtt cgttaatacg     300
gcaacaaata ctttctaccg tttttcagat tttacacata tatcagtgcc cggtgtgaca     360
acggtttcca tgacaacgga cagcagttat accactctgc aacgtgtcgc agcgctggaa     420

-continued

```
cgttccggaa tgcaaatcag tcgtcactca ctggtttcat catatctggc gttaatggag      480
ttcagtggta atacaatgac cagagatgca tccagagcag ttctgcgttt tgtcactgtc      540
acagcagaag ccttacgctt caggcagata cagagagaat tcgtcaggc actgtctgaa       600 actgctcctg tgtatacgat gacgccggga gacgtggacc tcactctgaa ctgggggcga      660
atcagcaatg tgcttccgga gtatcgggga gaggatggtg tcagagtggg gagaatatcc      720
tttaataata tatcggcgat actgggcact gtggccgtta tactgaattg tcatcatcag      780
ggggcgcgtt ctgttcgcgc cgtgaatgaa gagagtcaac cagaatgtca gataactggc      840
gacaggcccg ttataaaaat aaacaataca ttatgggaaa gtaatacagc tgcagcgttt      900
ctgaacagaa agtcacagtt tttatataca acgggtaaat aaaggagtta agtatgaaga      960
agatgtttat ggcggtttta tttgcattag tttctgttaa tgcaatggcg gcggattgcg     1020
ctaaaggtaa aattgagttt tccaagtata atgagaatga tacattcaca gtaaaagtgg     1080
ccggaaaaga gtactggacc agtcgctgga atctgcaacc gttactgcaa agtgctcagt     1140
tgacaggaat gactgtcaca attaaatcca gtacctgtga atcaggctcc ggatttgctg     1200
aagtgcagtt taataatgac tgaggcataa cctgattcgt ggtatgtggg taac           1254

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: primer for
      PCR

<400> SEQUENCE: 4
agccacatat aaattatttt g                                                21

<210> SEQ ID NO 5
<211> LENGTH: 285
<212> TYPE: DNA
<213> ORGANISM: Escherichia coli

<400> SEQUENCE: 5
aaatgggtac tgtgcctgtt actgggtttt ccttcggtat cctattcccg ggagtttatg       60
atagactttt cgacccaaca aagttatgtc tcttcgttaa atagtatacg gacagagata      120
tcgacccctc ttgaacatat atctcagggg accacatcgg tgtctgttat taaccacacc      180
ccaccgggca gttattttgc tgtggatata cgagggcttg atgtctatca ggcgcgtttt      240
gaccatcttc gtctgattat tgagcaaaat aatttatatg tggct                     285
```